United States Patent
Williams

(10) Patent No.: US 10,952,734 B2
(45) Date of Patent: Mar. 23, 2021

(54) STAPLING DEVICE WITH CUT RING BIASING MEMBER

(71) Applicant: Covidien LP, Mansfield, MA (US)

(72) Inventor: Justin Williams, Southbury, CT (US)

(73) Assignee: Covidien LP, Mansfield, MA (US)

(*) Notice: Subject to any disclaimer, the term of this patent is extended or adjusted under 35 U.S.C. 154(b) by 188 days.

(21) Appl. No.: 16/351,894

(22) Filed: Mar. 13, 2019

(65) Prior Publication Data
US 2019/0321046 A1  Oct. 24, 2019

Related U.S. Application Data

(60) Provisional application No. 62/661,224, filed on Apr. 23, 2018.

(51) Int. Cl.
*A61B 17/115* (2006.01)
*A61B 17/00* (2006.01)

(52) U.S. Cl.
CPC . *A61B 17/1155* (2013.01); *A61B 2017/00367* (2013.01); *A61B 2017/00473* (2013.01)

(58) Field of Classification Search
CPC .................................................. A61B 17/115
USPC ........................................................ 227/180.1
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |

(Continued)

FOREIGN PATENT DOCUMENTS

| | | |
|---|---|---|
| CA | 908529 A | 9/1972 |
| CA | 2805365 A1 | 8/2013 |

(Continued)

OTHER PUBLICATIONS

European Search Report dated Aug. 30, 2019, issued in EP Appln. No. 19170302.

*Primary Examiner* — Nathaniel C Chukwurah

(57) ABSTRACT

A circular stapling device includes a shell assembly and an anvil assembly. The shell assembly includes a housing, a staple cartridge supported on the housing, an annular knife supported within the housing, and a biasing member supported within the housing. The anvil assembly includes a center rod and an anvil head that supports a cut ring that is axially aligned with the annular knife. The biasing member is positioned within the housing and extends to a position distally of the annular knife when the annular knife is in the retracted position to shield the annular knife. The anvil assembly is movably supported in relation to the shell assembly between an unapproximated position and an approximated position, wherein in the approximated position, the biasing member is engaged with the cut ring and urges the cut ring in a distal direction.

19 Claims, 6 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A * | 9/1990 | Lipatov ............... A61B 17/115 227/180.1 |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A * | 8/1992 | Segato ............... A61B 17/115 227/179.1 |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A * | 12/1993 | Grant ............... A61B 17/115 227/179.1 |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A * | 5/1994 | Welch ............... A61B 17/0218 128/898 |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A * | 11/1995 | Chen ............... A61B 17/1114 606/153 |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 * | 7/2001 | Balazs ............... A61B 17/115 227/175.1 |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |

(56) References Cited

U.S. PATENT DOCUMENTS

| | | | |
|---|---|---|---|
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,551,334 B2 | 4/2003 | Blatter et al. | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,605,098 B2 | 8/2003 | Nobis et al. | |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,652,542 B2 | 11/2003 | Blatter et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,698,643 B2 | 3/2004 | Whitman | |
| 6,716,222 B2 | 4/2004 | McAlister et al. | |
| 6,716,233 B1 | 4/2004 | Whitman | |
| 6,726,697 B2 | 4/2004 | Nicholas et al. | |
| 6,742,692 B2 | 6/2004 | Hartwick | |
| 6,743,244 B2 | 6/2004 | Blatter et al. | |
| 6,763,993 B2 | 7/2004 | Bolduc et al. | |
| 6,769,590 B2 | 8/2004 | Vresh et al. | |
| 6,769,594 B2 | 8/2004 | Orban, III | |
| 6,820,791 B2 | 11/2004 | Adams | |
| 6,821,282 B2 | 11/2004 | Perry et al. | |
| 6,827,246 B2 | 12/2004 | Sullivan et al. | |
| 6,840,423 B2 | 1/2005 | Adams et al. | |
| 6,843,403 B2 | 1/2005 | Whitman | |
| 6,846,308 B2 | 1/2005 | Whitman et al. | |
| 6,852,122 B2 | 2/2005 | Rush | |
| 6,866,178 B2 | 3/2005 | Adams et al. | |
| 6,872,214 B2 | 3/2005 | Sonnenschein et al. | |
| 6,874,669 B2 | 4/2005 | Adams et al. | |
| 6,884,250 B2 | 4/2005 | Monassevitch et al. | |
| 6,905,504 B1 | 6/2005 | Vargas | |
| 6,938,814 B2 | 9/2005 | Sharma et al. | |
| 6,942,675 B1 | 9/2005 | Vargas | |
| 6,945,444 B2 | 9/2005 | Gresham et al. | |
| 6,953,138 B1 | 10/2005 | Dworak et al. | |
| 6,957,758 B2 * | 10/2005 | Aranyi | A61B 17/072 227/176.1 |
| 6,959,851 B2 | 11/2005 | Heinrich | |
| 6,978,922 B2 | 12/2005 | Bilotti et al. | |
| 6,981,941 B2 | 1/2006 | Whitman et al. | |
| 6,981,979 B2 | 1/2006 | Nicolo | |
| 7,032,798 B2 | 4/2006 | Whitman et al. | |
| 7,059,331 B2 | 6/2006 | Adams et al. | |
| 7,059,510 B2 | 6/2006 | Orban, III | |
| 7,077,856 B2 | 7/2006 | Whitman | |
| 7,080,769 B2 | 7/2006 | Vresh et al. | |
| 7,086,267 B2 | 8/2006 | Dworak et al. | |
| 7,114,642 B2 | 10/2006 | Whitman | |
| 7,118,528 B1 | 10/2006 | Piskun | |
| 7,122,044 B2 | 10/2006 | Bolduc et al. | |
| 7,128,748 B2 | 10/2006 | Mooradian et al. | |
| 7,141,055 B2 | 11/2006 | Abrams et al. | |
| 7,168,604 B2 | 1/2007 | Milliman et al. | |
| 7,179,267 B2 | 2/2007 | Nolan et al. | |
| 7,182,239 B1 | 2/2007 | Myers | |
| 7,195,142 B2 | 3/2007 | Orban, III | |
| 7,207,168 B2 | 4/2007 | Doepker et al. | |
| 7,220,237 B2 | 5/2007 | Gannoe et al. | |
| 7,234,624 B2 | 6/2007 | Gresham et al. | |
| 7,235,089 B2 | 6/2007 | McGuckin, Jr. | |
| RE39,841 E | 9/2007 | Bilotti et al. | |
| 7,285,125 B2 | 10/2007 | Viola | |
| 7,303,106 B2 | 12/2007 | Milliman et al. | |
| 7,303,107 B2 | 12/2007 | Milliman et al. | |
| 7,309,341 B2 | 12/2007 | Ortiz et al. | |
| 7,322,994 B2 | 1/2008 | Nicholas et al. | |
| 7,325,713 B2 | 2/2008 | Aranyi | |
| 7,334,718 B2 | 2/2008 | McAlister et al. | |
| 7,335,212 B2 | 2/2008 | Edoga et al. | |
| 7,364,060 B2 | 4/2008 | Milliman | |
| 7,398,908 B2 | 7/2008 | Holsten et al. | |
| 7,399,305 B2 | 7/2008 | Csiky et al. | |
| 7,401,721 B2 | 7/2008 | Holsten et al. | |
| 7,401,722 B2 | 7/2008 | Hur | |
| 7,407,075 B2 | 8/2008 | Holsten et al. | |
| 7,410,086 B2 | 8/2008 | Ortiz et al. | |
| 7,422,137 B2 | 9/2008 | Manzo | |
| 7,422,138 B2 | 9/2008 | Bilotti et al. | |
| 7,431,191 B2 | 10/2008 | Milliman | |
| 7,438,718 B2 | 10/2008 | Milliman et al. | |
| 7,455,676 B2 | 11/2008 | Holsten et al. | |
| 7,455,682 B2 | 11/2008 | Viola | |
| 7,481,347 B2 | 1/2009 | Roy | |
| 7,494,038 B2 | 2/2009 | Milliman | |
| 7,506,791 B2 | 3/2009 | Omaits et al. | |
| 7,516,877 B2 | 4/2009 | Aranyi | |
| 7,527,185 B2 | 5/2009 | Harari et al. | |
| 7,537,602 B2 | 5/2009 | Whitman | |
| 7,540,839 B2 | 6/2009 | Butler et al. | |
| 7,546,939 B2 | 6/2009 | Adams et al. | |
| 7,546,940 B2 | 6/2009 | Milliman et al. | |
| 7,547,312 B2 | 6/2009 | Bauman et al. | |
| 7,556,186 B2 | 7/2009 | Milliman | |
| 7,559,451 B2 | 7/2009 | Sharma et al. | |
| 7,585,306 B2 | 9/2009 | Abbott et al. | |
| 7,588,174 B2 | 9/2009 | Holsten et al. | |
| 7,600,663 B2 | 10/2009 | Green | |
| 7,611,038 B2 | 11/2009 | Racenet et al. | |
| 7,635,385 B2 | 12/2009 | Milliman et al. | |
| 7,669,747 B2 | 3/2010 | Weisenburgh, II et al. | |
| 7,686,201 B2 | 3/2010 | Csiky | |
| 7,694,864 B2 | 4/2010 | Okada et al. | |
| 7,699,204 B2 | 4/2010 | Viola | |
| 7,708,181 B2 | 5/2010 | Cole et al. | |
| 7,717,313 B2 | 5/2010 | Criscuolo et al. | |
| 7,721,932 B2 | 5/2010 | Cole et al. | |
| 7,726,539 B2 | 6/2010 | Holsten et al. | |
| 7,743,958 B2 | 6/2010 | Orban, III | |
| 7,744,627 B2 | 6/2010 | Orban, III et al. | |
| 7,770,776 B2 | 8/2010 | Chen et al. | |
| 7,771,440 B2 | 8/2010 | Ortiz et al. | |
| 7,776,060 B2 | 8/2010 | Mooradian et al. | |
| 7,793,813 B2 | 9/2010 | Bettuchi | |
| 7,802,712 B2 | 9/2010 | Milliman et al. | |
| 7,823,592 B2 | 11/2010 | Bettuchi et al. | |
| 7,837,079 B2 | 11/2010 | Holsten et al. | |
| 7,837,080 B2 | 11/2010 | Schwemberger | |
| 7,837,081 B2 | 11/2010 | Holsten et al. | |
| 7,845,536 B2 | 12/2010 | Viola et al. | |
| 7,845,538 B2 | 12/2010 | Whitman | |
| 7,857,187 B2 | 12/2010 | Milliman | |
| 7,886,951 B2 | 2/2011 | Hessler | |
| 7,896,215 B2 | 3/2011 | Adams et al. | |
| 7,900,806 B2 | 3/2011 | Chen et al. | |
| 7,909,039 B2 | 3/2011 | Hur | |
| 7,909,219 B2 | 3/2011 | Cole et al. | |
| 7,909,222 B2 | 3/2011 | Cole et al. | |
| 7,909,223 B2 | 3/2011 | Cole et al. | |
| 7,913,892 B2 | 3/2011 | Cole et al. | |
| 7,918,377 B2 | 4/2011 | Measamer et al. | |
| 7,922,062 B2 | 4/2011 | Cole et al. | |
| 7,922,743 B2 | 4/2011 | Heinrich et al. | |

(56) References Cited

U.S. PATENT DOCUMENTS

| | | |
|---|---|---|
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,023,014 B2 | 5/2015 | Chowaniec et al. |
| 9,055,943 B2 | 6/2015 | Zemlok et al. |
| 2003/0111507 A1 | 6/2003 | Nunez |
| 2004/0073090 A1 | 4/2004 | Butler et al. |
| 2005/0021053 A1 | 1/2005 | Heinrich |
| 2005/0051597 A1 | 3/2005 | Toledano |
| 2005/0107813 A1 | 5/2005 | Gilete Garcia |
| 2005/0205639 A1 | 9/2005 | Milliman |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |

(56) References Cited

U.S. PATENT DOCUMENTS

| | | |
|---|---|---|
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0263556 A1* | 9/2014 | Mozdzierz ....... A61B 17/07207 227/176.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2018/0271524 A1 | 9/2018 | Williams et al. |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2774551 A2 | 9/2014 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

STAPLING DEVICE WITH CUT RING BIASING MEMBER

CROSS-REFERENCE TO RELATED APPLICATIONS

This application claims the benefit of and priority to U.S. Provisional Patent Application No. 62/661,224 filed Apr. 23, 2018, the entire disclosure of which is incorporated by reference herein.

BACKGROUND

1. Technical Description

The present disclosure is directed to circular stapling devices and more particularly, to a shell assembly of a circular device with structure to facilitate separation of a knife and a cut ring after firing.

2. Background of Related Art

Circular stapling devices for performing end-to-end or end-to-side anastomosis procedures are well known. Typically, circular stapling devices include a staple cartridge that supports a plurality of staples, a pusher that is movable in relation to the staple cartridge to eject the staples from the staple cartridge, an annular knife that is movable to core tissue within the anastomosis, and an anvil assembly that is positioned to deform the staples. In embodiments, the anvil includes a cut ring that provides a back stop for the annular knife.

In known stapling devices, the anvil assembly includes an anvil head that is pivotal from an operative position to a tilted position to reduce a profile of the anvil assembly for subsequent removal of the anvil assembly from a patient. In such stapling devices, the cut ring is movable in response to engagement by the annular knife from a first position that prevents movement of the anvil head from the operative position to the tilted position to a second position that allows for pivotal movement of the anvil head from the operative position to the tilted position. When the annular knife is advanced into the cut ring of the anvil assembly during firing of the stapling device, the annular knife urges the cut ring from the first position to the second position to facilitate tilting of the anvil head.

Typically, the cut ring is formed in part from a material that is softer than the annular knife such that the annular knife penetrates the cut ring during firing of the stapling device. In some instances, the annular knife sticks to the cut ring and the cut ring is moved back to its first position when the annular knife is retracted to a pre-fired position after firing. When this happens, the anvil head is prevented from moving to the tilted position after firing.

A continuing need exists in the art for an improved shell assembly for a circular stapling device that includes a simple device or mechanism that ensures separation of the annular knife and cut ring after firing of the stapling device to facilitate movement of the anvil head to the tilted position during removal of the stapling device from a patient.

SUMMARY

One aspect of the present disclosure is directed to a circular stapling device having an elongate body, a shell assembly, and an anvil assembly. The elongate body has a proximal portion and a distal portion. The shell assembly includes a housing, a staple cartridge supported on the housing, an annular knife supported within the housing, and a biasing member supported within the housing. The biasing member has a proximal portion and a distal portion. The annular knife is movable within the housing from a retracted position to an advanced position and extends from the distal portion of the housing in the advanced position. The biasing member extends to a position distally of the annular knife when the annular knife is in the retracted position. The anvil assembly includes a center rod and an anvil head that supports a cut ring that is axially aligned with the annular knife. The anvil assembly is movably supported in relation to the shell assembly between an unapproximated position and an approximated position, wherein in the approximated position, the biasing member is engaged with the cut ring and urges the cut ring in a distal direction.

Another aspect of the present disclosure is directed to a shell assembly including a housing, a staple cartridge, an annular knife, and a biasing member. The housing has a proximal portion and a distal portion and defines an annular channel. The staple cartridge is supported on the housing. The shell assembly defines a plurality of staple receiving pockets that support staples. The annular knife is supported within the housing and is movable within the housing from a retracted position to an advanced position. The annular knife extends from the distal portion of the housing when the annular knife is in the advanced position. The biasing member is supported within the annular channel of the housing and extends to a position distally of the annular knife when the annular knife is in the retracted position.

In embodiments, the biasing member is a coil spring.

In some embodiments, the shell assembly includes a pusher assembly including a pusher having a plurality of fingers, wherein the pusher is movable from a retracted position to an advanced position to eject staples from the staple cartridge.

In certain embodiments, the shall assembly includes a knife carrier that supports the annular knife and is movable from a retracted position to an advanced position within the housing, wherein the annular knife engages the cut ring when the anvil assembly and the shell assembly are in the approximated position and the annular knife is in the advanced position.

In embodiments, the annular knife includes a cutting edge that is positioned distally of the biasing member when the annular knife is in the advanced position.

In some embodiments, the biasing member is secured to the knife carrier.

In certain embodiments, the knife carrier defines a retaining groove that receives a coil of the coil spring to secure the biasing member to the knife carrier.

In embodiments, the stapling device includes a handle assembly and the elongate body extends distally from the handle assembly.

In some embodiments, the shell assembly includes a knife carrier that supports the annular knife, and the knife carrier is movable from a retracted position to an advanced position within the housing independently of the pusher.

In certain embodiments, the housing defines an annular channel, and the pusher and the knife carrier are movably supported within the annular channel.

In embodiments, the biasing member is positioned within the annular knife.

BRIEF DESCRIPTION OF THE DRAWINGS

Various embodiments of the presently disclosed circular stapling device are described herein below with reference to the drawings, wherein.

DETAILED DESCRIPTION OF EMBODIMENTS

Figure 1:
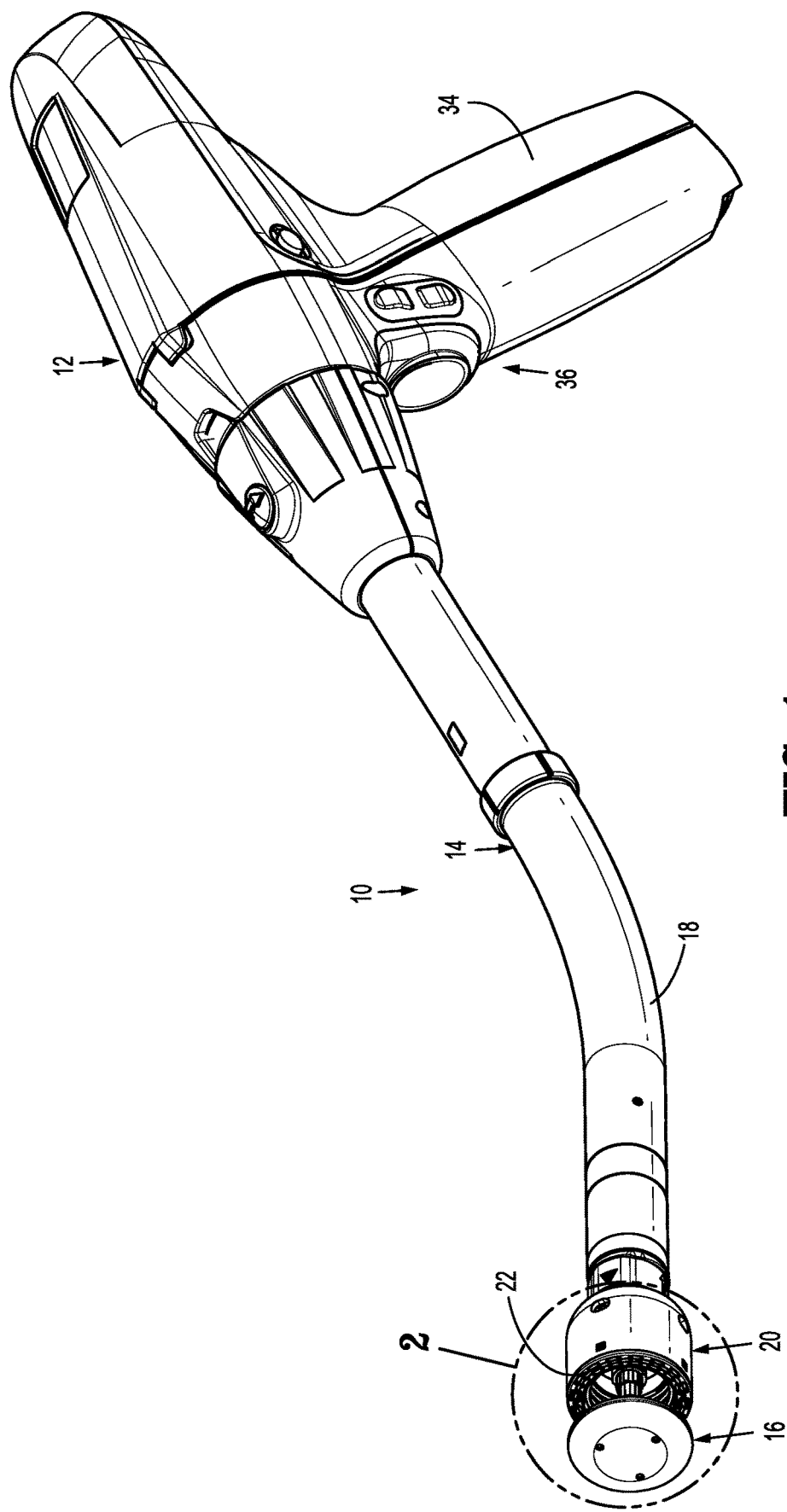
FIG. 1 is a side perspective view of an exemplary embodiment of the presently disclosed circular stapling device in an unapproximated position.

The presently disclosed circular stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 2:
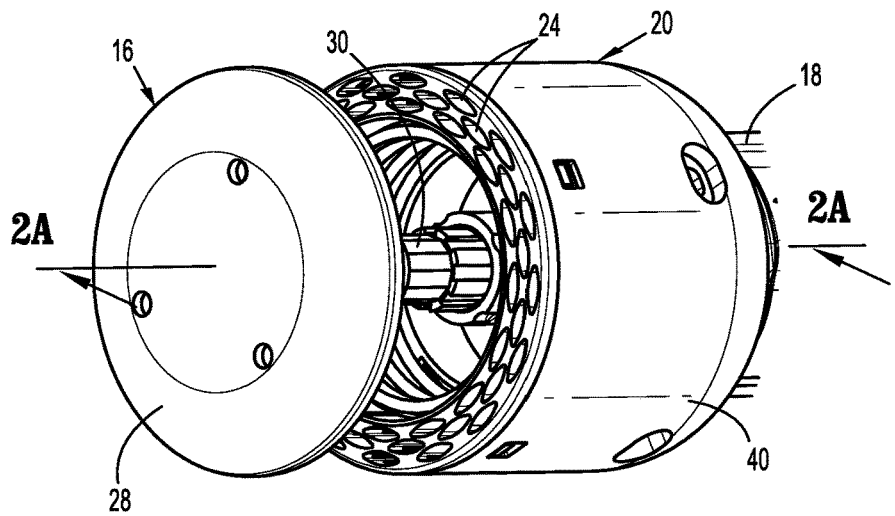
FIG. 2 is an enlarged view of the indicated area of detail shown in FIG. 1.
Figure 2A:
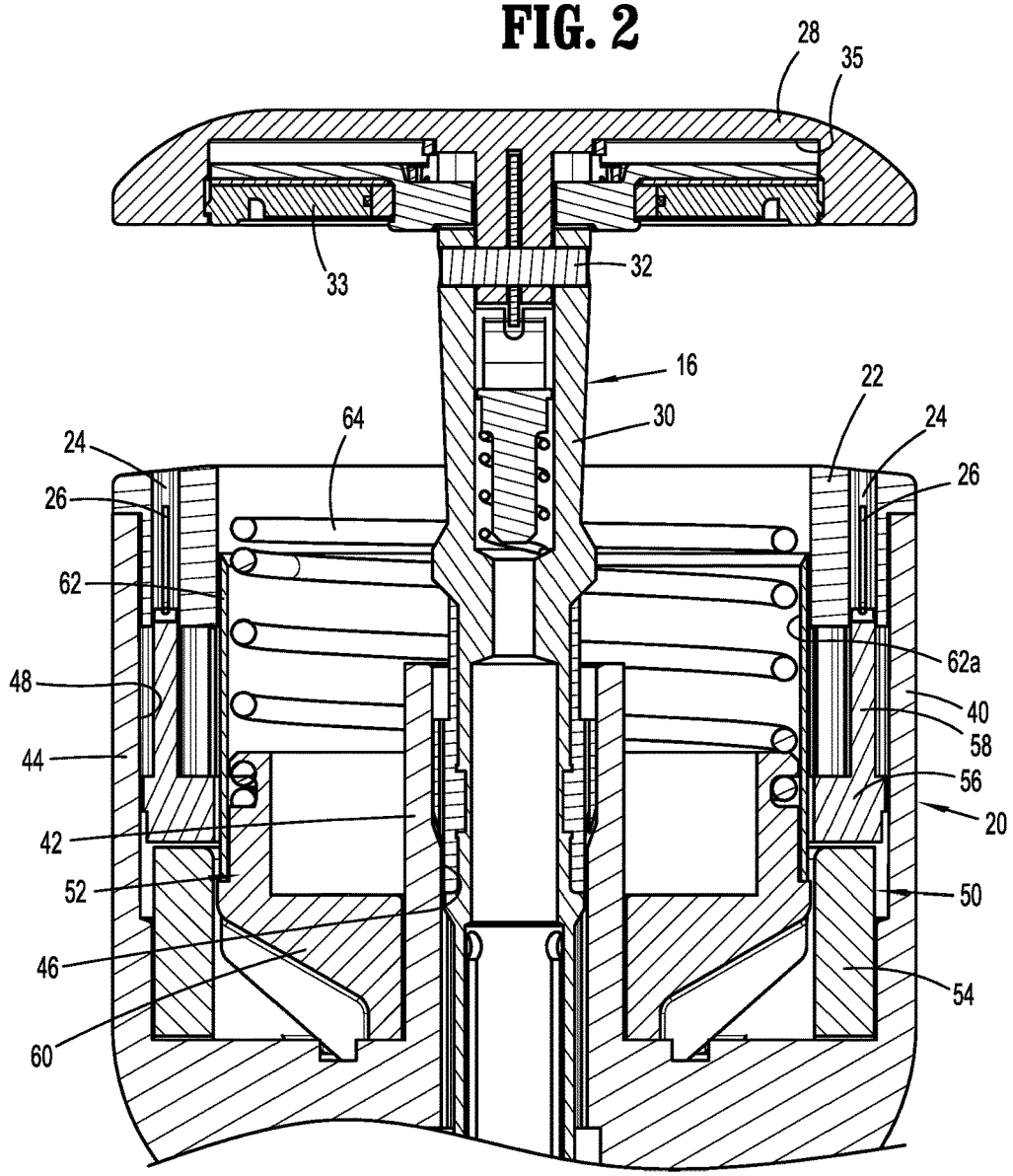
FIG. 2A is a cross-sectional view taken along section line 2A-2A of FIG. 2.
Figure 7:
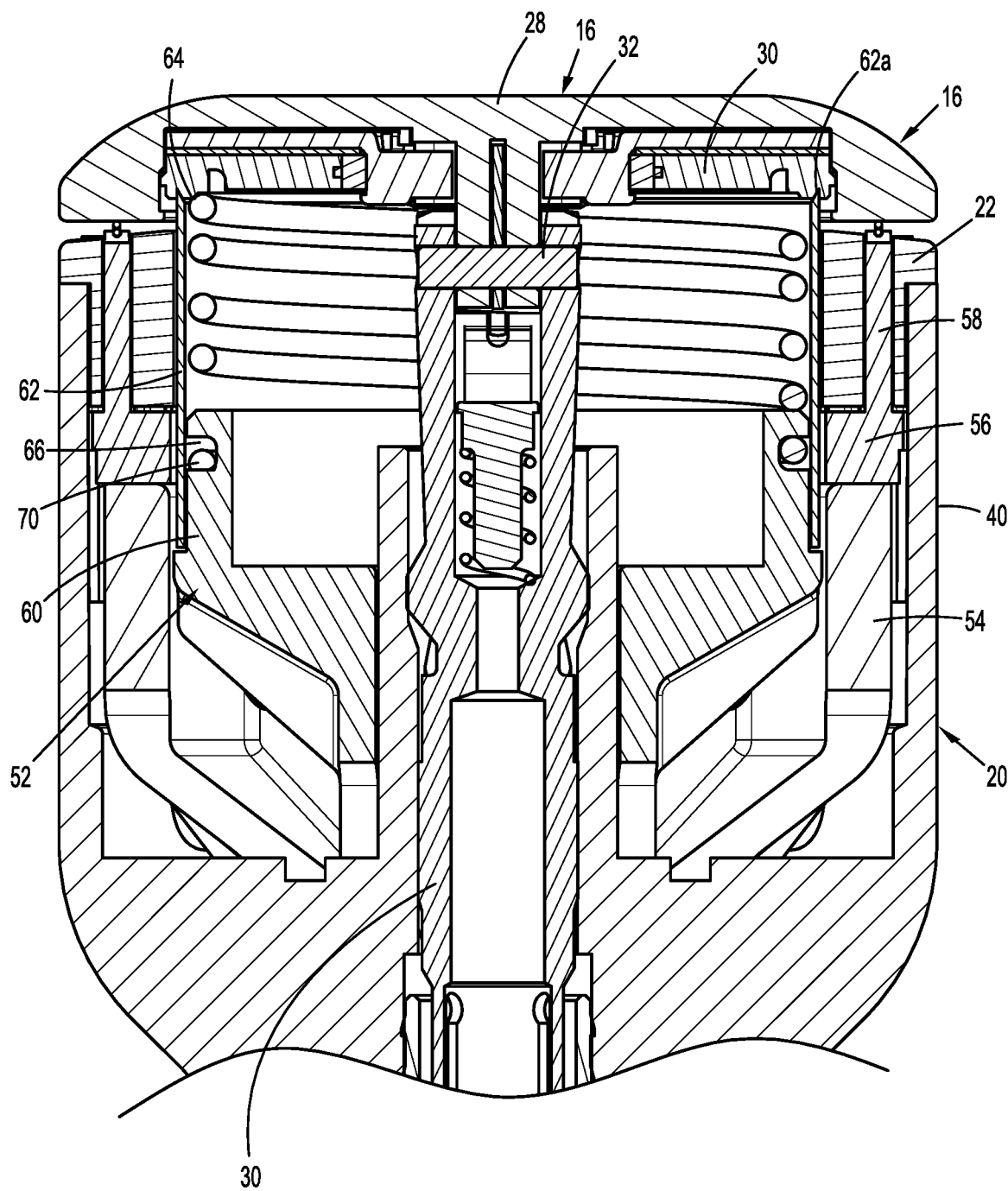
FIG. 7 is a side cross-sectional view of the shell assembly of the circular stapling device shown in FIG. 1 with the tool assembly in an approximated, fired condition.

FIGS. 1-2A illustrate an exemplary embodiment of the presently disclosed circular stapling device shown generally as stapling device 10. The stapling device 10 includes a handle assembly 12, an elongate body or adaptor assembly 14, and an anvil assembly 16. The adaptor assembly 14 includes an elongate body 18 and a shell assembly 20. The shell assembly 20 has a proximal portion supported on a distal portion of the elongate body 18 and a distal portion that supports a staple cartridge 22. The staple cartridge 22 defines a plurality of annular rows of staple receiving pockets 24. Each of the staple receiving pockets 24 receives a staple 26 (FIG. 2A) such that the staple cartridge 20 supports annular rows of staples 26. The anvil assembly 16 includes a head 28 and a center rod 30. The anvil head 28 is supported on a distal end of the anvil center rod 30 by a pivot member 32 (FIG. 2A) and supports a cut ring 33 (FIG. 2A). The cut ring 33 is movable within a recess 35 (FIG. 2A) defined within the anvil head 28 from a retracted position (FIG. 2A) to an advanced position (FIG. 7.) As is known in the art, in the retracted position, the cut ring 33 prevents tilting of the anvil head 28 in relation to the center rod 30, and in the advanced position, the cut ring 33 allows tilting of the anvil head 28 in relation to the center rod 30. See, e.g., U.S. Pat. No. 7,303,106 ("the '106 patent") for a detailed description of exemplary embodiments of an anvil assembly with a tiltable anvil assembly. The '106 patent is incorporated herein by reference in its entirety.

The handle assembly 12 is illustrated as a powered assembly and includes a stationary grip 34 (FIG. 1) and actuation buttons 32 for controlling operation of stapling device functions including approximation of the anvil and shell assemblies 16, 20, respectively, and firing of staples 26 (FIG. 2A) from the staple cartridge 22 of the shell assembly 20. The adaptor assembly 14 is coupled to the handle assembly 12 to translate power from the handle assembly 12 to the anvil and shell assemblies 16, 20. Although the present disclosure illustrates powered handle and adaptor assemblies 12, 14, respectively, it is envisioned that the advantages of the present disclosure as described in detail below are also applicable to circular stapling devices having manually operated handle and adaptor assemblies. The '106 patent discloses an example of a surgical stapling device including a manually actuated handle assembly and is incorporated herein by reference in its entirety. U.S. Pat. No. 9,023,014 ("the '014 patent") and U.S. Pat. No. 9,055,943 ("the '943 patent") disclose examples of surgical stapling devices including exemplary powered handle and adaptor assemblies. Each of these patents is incorporated herein by reference in its entirety.

Figure 3:
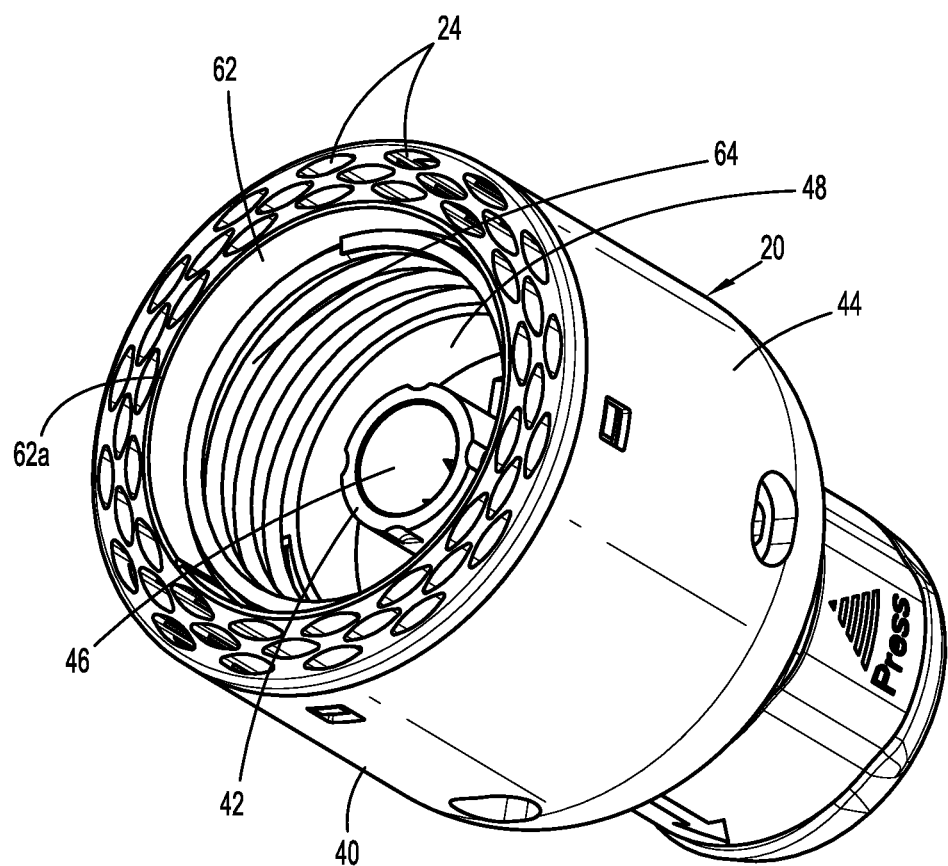
FIG. 3 is a side perspective view from the distal end of the shell assembly of the circular stapling device shown in FIG. 1.

Referring to FIGS. 2-3, the shell assembly 20 includes a housing 40 having an inner housing portion 42 (FIG. 2A) and an outer housing portion 44. The inner housing portion 42 defines a central through bore 46. The central through bore 46 receives an anvil retainer (not shown) of the adaptor assembly 14 and the anvil center rod 30 when the stapling device 10 is approximated as is known in the art. The inner housing portion 42 and the outer housing portion 44 of the housing portion 44 define an annular channel 48.

The shell assembly 20 also includes a pusher assembly 50 and a knife assembly 52. The pusher assembly 50 and the knife assembly 52 are supported within the annular channel 48 of the shell housing 40 for movement between a retracted position (FIG. 2A) and an advanced position (FIG. 7). The pusher assembly 50 includes a pusher back 54 and a pusher 56. The pusher back 54 includes a proximal end that is coupled to the adaptor assembly 14 and a distal end that is in abutting relation to the pusher 56. The pusher 56 includes fingers 58 that are received within the staple receiving pockets 24 of the staple cartridge 22 and engage the staples 26. When the adaptor assembly 14 is driven to advance the pusher assembly 50 within the annular channel 48 of the shell housing 40, the fingers 58 of the pusher 56 are advanced through the staple receiving pockets 24 of the staple cartridge 22 to fire the staples 26 from the staple cartridge 22.

Figure 4:
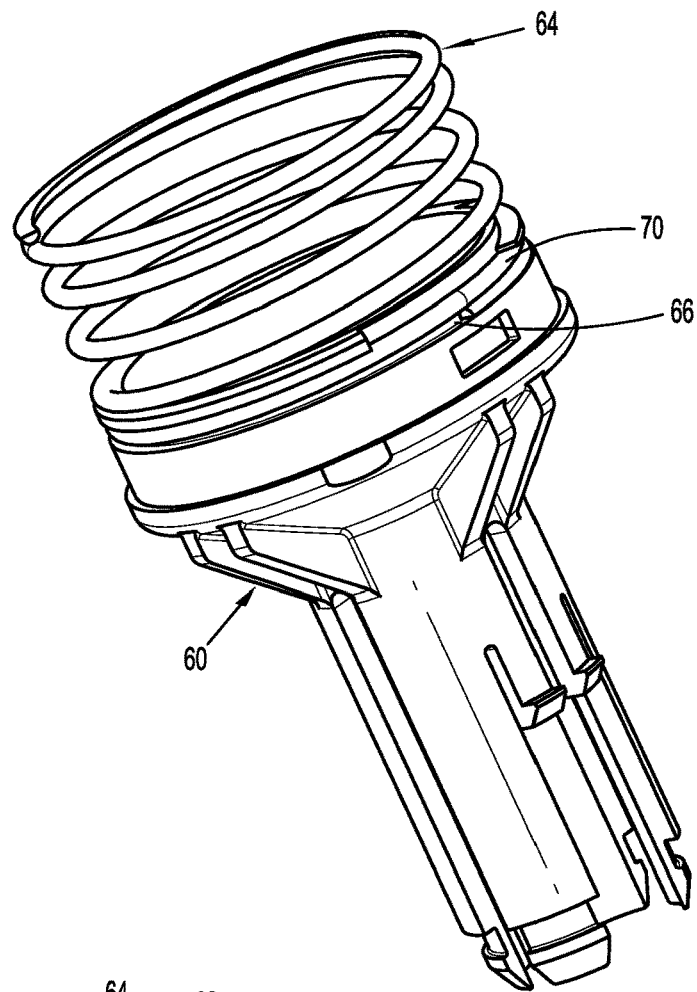
FIG. 4 is a side perspective view of the knife carrier assembly of the circular stapling device shown in FIG. 1 with the annular knife removed.
Figure 5:
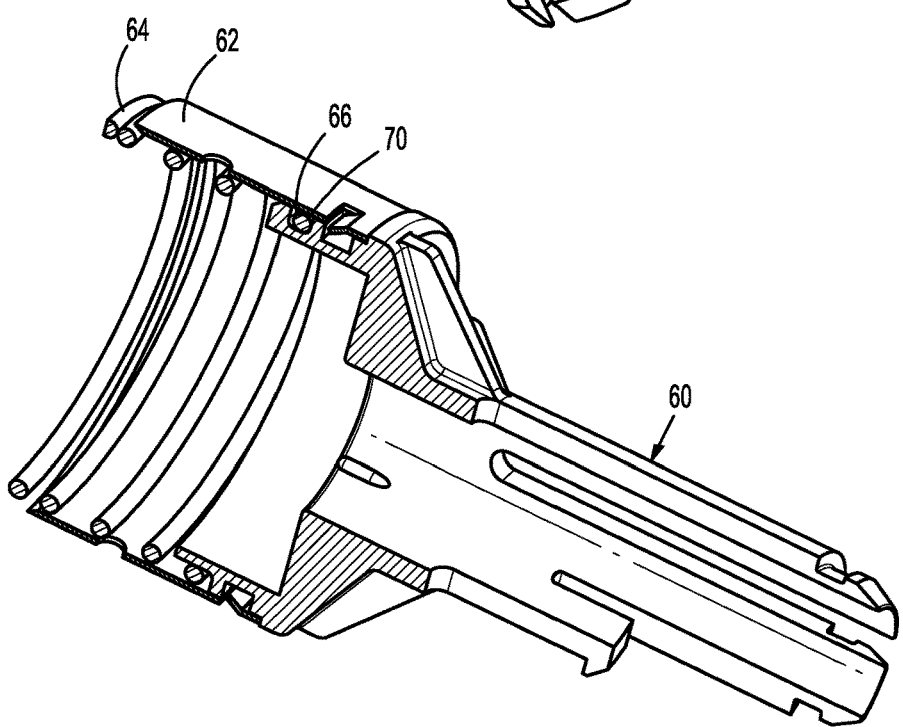
FIG. 5 is a side cross-sectional view of the knife carrier assembly of the circular stapling device shown in FIG. 1.
Figure 6:
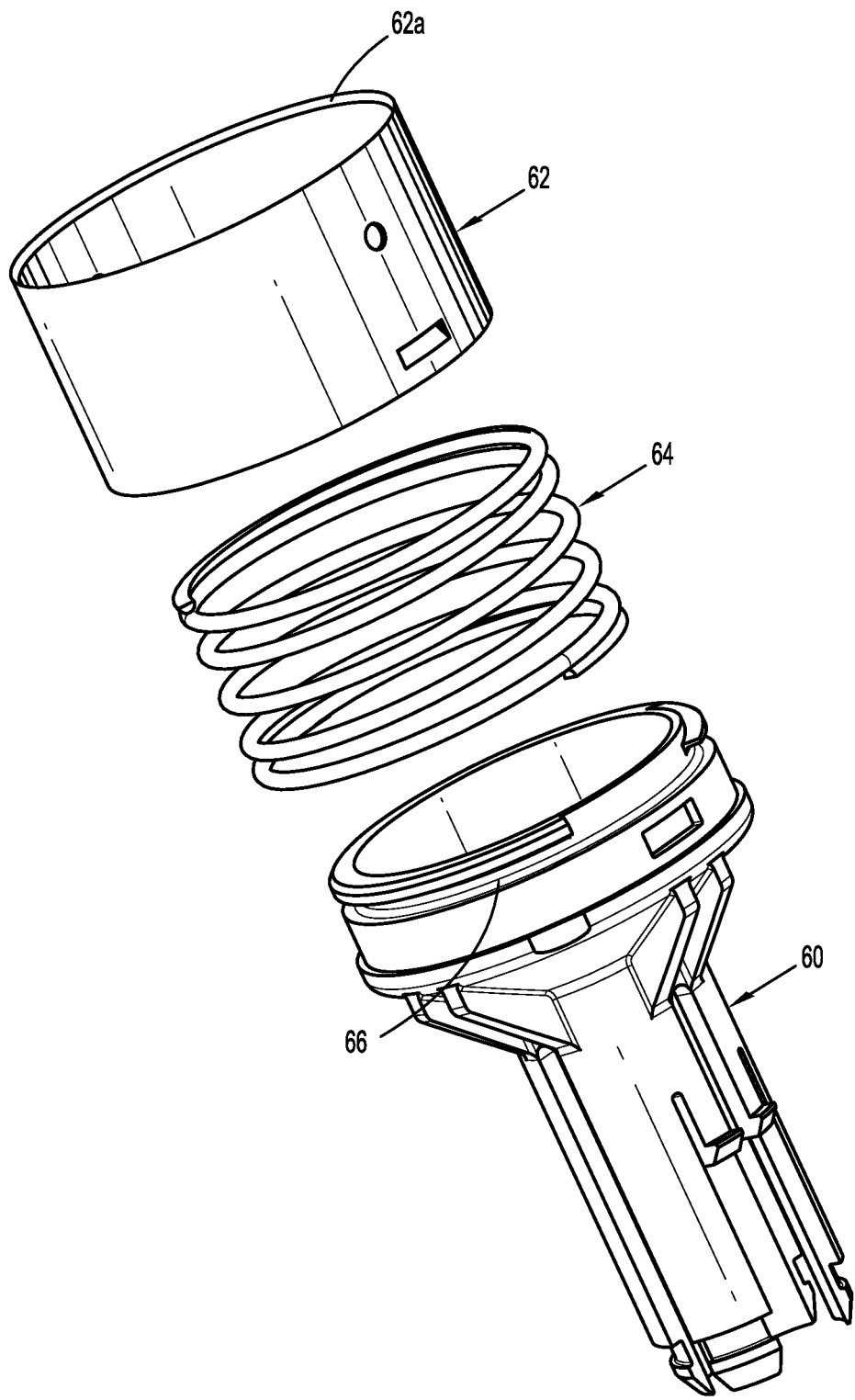
FIG. 6 is an exploded view of the knife carrier assembly shown in FIG. 5.

Referring also to FIGS. 4-6, the knife assembly 52 includes a knife carrier 60 and an annular knife blade 62. The knife carrier 60 includes a proximal end that is coupled to the adaptor assembly 14 and a distal end that supports the annular knife blade 62. In embodiments, the annular knife 62 includes a cutting edge 62a. The annular knife 62 is axially aligned with the cut ring 33 of the anvil head 28 of the anvil assembly 16. When the adaptor assembly 14 is driven to advance the knife carrier 60 within the annular channel 48 of the shell housing 40, the annular knife blade 62 is advanced into the cut ring 33 of the anvil assembly 16. For a more detailed description of the interconnection of the adaptor assembly 14 and the pusher and knife assemblies 50, 52 of a circular stapling device, see U.S. patent application Ser. No. 15/467,153 which is incorporated herein by reference in its entirety.

The knife assembly 52 also includes a biasing member 64 that is positioned on the distal portion of the knife carrier 60 and extends along an internal surface 62*a* (FIG. 2A) of the knife blade 62. In an unbiased state of the biasing member 64, a distal end of the biasing member 64 is positioned distally of the distal end of the annular knife blade 62 (FIG. 5) to shield the end of the knife blade 62 from a clinician. The biasing member 64 is in an unbiased state when the stapling device 10 is in an unapproximated state (FIG. 2A.)

In embodiments, the biasing member 64 is a coil spring and the knife carrier 60 includes an annular retainer groove 66 (FIG. 5). The annular retainer groove 66 is configured to receive a coil 70 at a proximal end of the biasing member 64 to secure the biasing member 64 to the knife carrier 60. As described above, the annular knife blade 62 is positioned about the biasing member 64 in a position to prevent separation of the coil 70 from the retaining groove 66.

Referring to FIG. 7, when the anvil assembly 16 and the shell assembly 20 are approximated, the distal end of the biasing member 64 is in contact with the cut ring 33. When the stapling device 10 is fired, the biasing member 64 and the annular knife 62 are advanced into the cut ring 33 to compress the biasing member 64 such that the distal end of the annular knife 62 moves distally beyond the distal end of the biasing member 64 and penetrates the cut ring 33 of the anvil assembly 16. When the knife assembly 52 is in the advanced position within the housing 40 of the shell assembly 20, the biasing member 64 is compressed between the cut ring 33 of the anvil assembly 16 and the knife carrier 60 to urge the knife assembly 52 to the retracted position and to urge the cut ring 33 to the advanced position. When the knife assembly 52 is retracted after firing of the stapling device 10, the biasing member 64 minimizes the likelihood that the cut ring 33 will stick to the annular knife 62 and be returned to its retracted position (FIG. 2A). As discussed above, if the cut ring 33 returns to its first position, the anvil head 28 may be prevented from moving to a tilted reduced profile position after firing.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A circular stapling device comprising:
   an elongate body having a proximal portion and a distal portion;
   a shell assembly including a housing, a staple cartridge supported on the housing, an annular knife supported within the housing, and a biasing member supported within the housing, the biasing member having a proximal portion and a distal portion, the annular knife being movable within the housing from a retracted position to an advanced position and extending from the distal portion of the housing in the advanced position, the biasing member extending to a position distally of the annular knife when the annular knife is in the retracted position; and
   an anvil assembly including a center rod and an anvil head, the anvil head supporting a cut ring that is axially aligned with the annular knife, the anvil assembly being movably supported in relation to the shell assembly between an unapproximated position and an approximated position;
   wherein in the approximated position, the biasing member is engaged with the cut ring and urges the cut ring in a distal direction.

2. The circular stapling device of claim 1, wherein the biasing member is a coil spring.

3. The circular stapling device of claim 2, wherein the shell assembly includes a pusher assembly, the pusher assembly including a pusher having a plurality of fingers, that is movable from a retracted position to an advanced position to eject staples from the staple cartridge.

4. The circular stapling device of claim 3, wherein the shell assembly includes a knife carrier that supports the annular knife, the knife carrier being movable from a retracted position to an advanced position within the housing independently of the pusher.

5. The circular stapling device of claim 4, wherein the housing defines an annular channel, the pusher and the knife carrier being movably supported within the annular channel.

6. The circular stapling device of claim 2, wherein the shall assembly includes a knife carrier that supports the annular knife, the knife carrier being movable from a retracted position to an advanced position within the housing, the annular knife engaging the cut ring when the anvil assembly and the shell assembly are in the approximated position and the annular knife is in the advanced position.

7. The circular stapling device of claim 6, wherein the biasing member is secured to the knife carrier.

8. The circular stapling device of claim 7, wherein the knife carrier defines a retaining groove, the retaining groove receiving a coil of the coil spring to secure the biasing member to the knife carrier.

9. The circular stapling device of claim 2, wherein the biasing member is positioned within the annular knife.

10. The circular stapling device of claim 1, wherein the annular knife includes a cutting edge that is positioned distally of the biasing member when the annular knife is in the advanced position.

11. The circular stapling device of claim 1, further including a handle assembly, the elongate body extending distally from the handle assembly.

12. A shell assembly comprising:
   a housing having a proximal portion and a distal portion and defining an annular channel;
   a staple cartridge supported on the housing, the shell assembly defining a plurality of staple receiving pockets, each of the staple receiving pockets having a staple;
   an annular knife supported within the housing, the annular knife being movable within the housing from a retracted position to an advanced position, the annular knife extending from the distal portion of the housing when the annular knife is in the advanced position; and
   a biasing member supported within the annular channel of the housing, the biasing member extending to a position distally of the annular knife when the annular knife is in the retracted position.

13. The shell assembly of claim 12, wherein the biasing member is a coil spring.

14. The shell assembly of claim 13, wherein the coil spring is positioned within the annular knife.

15. The shell assembly of claim 14, wherein the shell assembly includes a pusher assembly, the pusher assembly including a pusher having a plurality of fingers that is movable from a retracted position to an advanced position to eject staples from the staple cartridge.

16. The shell assembly of claim 15, wherein the shell assembly includes a knife carrier that supports the annular knife, the knife carrier being movable from a retracted position to an advanced position within the housing.

17. The shell assembly of claim 16, wherein the cutting edge of the annular knife is positioned distally of the biasing member when the annular knife is in the advanced position.

18. The shell assembly of claim 16, wherein the biasing member is secured to the knife carrier.

19. The shell assembly of claim 18, wherein the knife carrier defines a retaining groove, the retaining groove receiving a coil of the coil spring to secure the biasing member to the knife carrier.

\* \* \* \* \*